United States Patent
Vogel et al.

(10) Patent No.: US 10,555,877 B2
(45) Date of Patent: Feb. 11, 2020

(54) LIGHT-CURING DENTAL COMPOSITES WITH INCREASING OPACITY

(71) Applicant: Ivoclar Vivadent AG, Schaan (LI)

(72) Inventors: Karin Vogel, Gamprin (LI); Sven Tauscher, Buchs SG (CH); Norbert Moszner, Mauren (LI)

(73) Assignee: Ivoclar Vivadent AG, Schaan (LI)

( * ) Notice: Subject to any disclaimer, the term of this patent is extended or adjusted under 35 U.S.C. 154(b) by 76 days.

(21) Appl. No.: 15/502,568

(22) PCT Filed: Aug. 19, 2015

(86) PCT No.: PCT/EP2015/069096
§ 371 (c)(1),
(2) Date: Feb. 8, 2017

(87) PCT Pub. No.: WO2016/026915
PCT Pub. Date: Feb. 25, 2016

(65) Prior Publication Data
US 2017/0224591 A1   Aug. 10, 2017

(30) Foreign Application Priority Data
Aug. 19, 2014   (EP) .................................... 14181463

(51) Int. Cl.
| | | |
|---|---|---|
| *A61K 6/083* | (2006.01) | |
| *A61K 6/00* | (2020.01) | |
| *A61C 5/20* | (2017.01) | |
| *A61C 5/77* | (2017.01) | |
| *A61C 5/30* | (2017.01) | |
| *A61C 13/00* | (2006.01) | |
| *A61C 13/15* | (2006.01) | |
| *A61K 6/04* | (2006.01) | |

(52) U.S. Cl.
CPC .............. *A61K 6/0835* (2013.01); *A61C 5/20* (2017.02); *A61C 5/30* (2017.02); *A61C 5/77* (2017.02); *A61C 13/0003* (2013.01); *A61C 19/003* (2013.01); *A61K 6/0005* (2013.01); *A61K 6/0008* (2013.01); *A61K 6/0038* (2013.01); *A61K 6/0052* (2013.01); *A61K 6/0091* (2013.01); *A61K 6/043* (2013.01); *A61K 6/083* (2013.01)

(58) Field of Classification Search
CPC ................................................... A61K 6/0005
See application file for complete search history.

(56) References Cited

U.S. PATENT DOCUMENTS

| | | | |
|---|---|---|---|
| 4,291,047 A | 9/1981 | Kranz et al. | |
| 4,447,520 A | 5/1984 | Henne et al. | |
| 4,737,593 A | 4/1988 | Ellrich et al. | |
| 5,534,559 A | 7/1996 | Leppard et al. | |
| 6,300,389 B1 * | 10/2001 | Sato ..................... | A61K 6/0005 106/36 |
| 9,532,930 B2 | 1/2017 | Burtscher et al. | |
| 2006/0178469 A1 | 8/2006 | Moszner et al. | |
| 2008/0076847 A1 | 3/2008 | Moszner et al. | |
| 2008/0319104 A1 | 12/2008 | Klapdohr et al. | |
| 2009/0298966 A1 | 12/2009 | Vanini et al. | |
| 2013/0203884 A1 | 8/2013 | Blomker et al. | |
| 2014/0206792 A1 * | 7/2014 | Ishizaka ............... | A61K 6/0005 523/115 |

FOREIGN PATENT DOCUMENTS

DE     202008018436 U1    11/2013

OTHER PUBLICATIONS

International Preliminary Report on Patentability of PCT/EP2015/069096, dated Feb. 21, 2017, 11 pages.
Elias, H.-G., "Polymers in optics and optoelectronics," Applications of Polymers, pp. 513-515, Weinheim 2003.
Braga, Roberto R., "Factors involved in the development of polymerization shrinkage stress in resin-composites: A systematic review," Academy of Dental Materials, 2005, 21, pp. 962-970, Elsevier Ltd.

* cited by examiner

*Primary Examiner* — Michael F Pepitone
(74) *Attorney, Agent, or Firm* — Ann M. Knab; Thad McMurray

(57) ABSTRACT

Radically polymerizable dental material which contains (a) at least one polyfunctional radically polymerizable monomer, (b) at least one further radically polymerizable monomer which can be monofunctional or polyfunctional, (c) at least one photoinitiator for the radical polymerization and (d) at least one filler. The material is characterized in that the mixture of the monomers (a) and (b) has a refractive index of from 1.50 to 1.70 and in that the refractive index of the monomer mixture before the curing corresponds to the refractive index of the filler used or is higher by up to 0.013 and after the curing is higher than the refractive index of the filler by at least 0.02.

15 Claims, No Drawings

LIGHT-CURING DENTAL COMPOSITES WITH INCREASING OPACITY

CROSS-REFERENCE TO RELATED APPLICATIONS

This application is a National Stage application of International patent application PCT/EP2015/076545 filed on Nov. 13, 2015, which claims priority to European patent application No. 14193336.6 filed on Nov. 13, 2014, the disclosures of which are incorporated herein by reference in their entirety.

TECHNICAL FIELD

The present invention relates to light-curing composites for use as dental cements and filling composites.

BACKGROUND OF THE INVENTION

Dental materials which are used e.g. as cement or as direct filling material generally contain a polymerizable organic matrix and one or more fillers, which are usually surface-modified with a polymerizable adhesion promoter. The filler content depends decisively on the intended use and can be up to 90 wt.-%, wherein fixing cements have a lower level of filling compared with filling materials. The polymerizable organic matrix usually contains a mixture of resin monomers, initiator components, stabilizers and pigments. Dental materials which contain a polymerizable matrix and filler are called composites. The polymerizable matrix is also called resin.

Mixtures of dimethacrylates are usually used as monomers. Widely used examples of these are the highly viscous dimethacrylates 2,2-bis[4-(2-hydroxy-3-methacryloyloxy-propyl)-phenyl]propane (bis-GMA) and 1,6-bis-[2-methacryloyloxy-ethoxycarbonylamino]-2,2,4-trimethylhexane (UDMA) and the dimethacrylates of lower viscosity, used as diluting monomers, bis-(3-methacryloyloxymethyl)tricycle [5.2.1.0$^{2,6}$]decane (TCP), decanediol-1,10-dimethacrylate (D$_3$MA) and triethylene glycol dimethacrylate (TEGDMA). During polymerization, dimethacrylates bring about a three-dimensional cross-linking of the polymer chains that form and thus result in an improved mechanical stability.

The materials usually also contain an initiator for the radical polymerization, wherein light-curing materials which contain a photoinitiator occupy a dominant position in dental filling therapy today.

A disadvantage of light-curing materials is that in particular the fitting of larger fillings is associated with a considerable outlay, because the light required for curing can only penetrate into the materials up to a limited depth. In the so-called incremental technique, the filling is therefore built up of the composite material in layers, wherein the layers have a thickness of approx. 2 mm in each case and are cured individually.

Recently, so-called "bulk fill" composites, which allow layer thicknesses of from 4 to 5 mm, have attracted a great deal of interest due to the possible time saving. A large through-curing depth is a prerequisite for the clinical suitability of these materials. This correlates with, among other things, the translucence of the materials, wherein the translucence is decisively influenced by the refractive indices of the resin matrix and of the fillers. In composites, a high translucence and thus a good through-curing depth can be achieved when the organic matrix and the fillers used have matching refractive indices.

Bulk fill filling composites currently used are characterized by a high translucence before and after curing. This is an advantage with regard to the through-curing depth, but a disadvantage of this is that, due to the high translucence, the composites poorly mask the dentine lying below them, which is undesirable for aesthetic reasons because the colour of the dentine differs from that of the visible tooth enamel.

A further problem is the polymerization shrinkage stress (PCS) which builds up during polymerization and increases as the layer thickness increases. A further difficulty is that the PCS is particularly high during the light curing (Braga et al., Dent. Mater. 21 (2005) 962-970).

SUMMARY OF THE INVENTION

The object of the invention is to provide light-curing dental materials, with large through-curing depth, which have a high masking power after the curing, have a translucence which is comparable to natural tooth substance and are also suitable for the restoration of teeth in the visible region of the mouth. In addition, the materials are to be curable in a short time and have a polymerization shrinkage which is as small as possible and a low PCS.

DETAILED DESCRIPTION

The object is achieved according to the invention by radically polymerizable dental materials which contain
(a) at least one polyfunctional radically polymerizable monomer,
(b) at least one further radically polymerizable monomer which can be monofunctional or polyfunctional,
(c) at least one photoinitiator for the radical polymerization and
(d) at least one filler.

The materials are characterized in that the mixture of the monomers (a) and (b) has a refractive index $n_D$ of from 1.50 to 1.70, preferably 1.50 to 1.60, and in that the refractive index of the monomer mixture before the curing corresponds to the refractive index of the filler (d) or is higher by up to 0.013 and after the curing is higher than the refractive index of the filler (d) by at least 0.02. In the uncured state, the materials preferably have the form of a paste. The mixture of the monomers (a) and (b) is also designated as matrix in the following.

The material can contain a filler mixture as filler (d), wherein filler (d) includes all fillers with a refractive index lying in the range of $n_D^{matrix} - n_D^{filler(d)} = 0$ to 0.013 ($n_D^{matrix}$=refractive index of the uncured monomer mixture).

The dental materials according to the invention have a high translucence before the polymerization because the refractive index of the monomers and that of the filler only differ slightly from each other. The light used for polymerization can therefore penetrate deep into the materials, which guarantees a large through-curing depth. During polymerization, the refractive index of the monomers increases, while the refractive index of the filler(s) remains unchanged. The difference between the refractive index of the monomers and that of the filler thereby grows, and the translucence decreases correspondingly. The monomers are selected such that the refractive index of the monomer mixture before the curing is higher than the refractive index of the filler by 0 to 0.13 and after the curing by at least 0.02, preferably by 0.020 to 0.045.

The refractive index of natural tooth enamel is approx. 1.62-1.66, and the refractive index of the dentine lying below the tooth enamel is approx. 1.45. The translucence of the tooth results from the overall impression of the highly transparent, thin enamel layer and the dentine. The materials according to the invention preferably have a translucence of from 5 to 15% after the curing. It was found that such materials come very close to the appearance of natural tooth substance and simultaneously make an optically satisfactory masking of the dentine possible. The materials thus allow an aesthetically satisfactory treatment of tooth defects even in the visible region of the mouth of a patient. The translucence of the materials can, as described in more detail below, be determined using a spectrophotometer.

In the preparation of radically polymerizable dental materials, polyfunctional monomers are primarily used to guarantee a high mechanical strength. However, these have the disadvantage that the viscosity increases rapidly due to the formation of a three-dimensional network, with the result that the polymerization shrinkage can no longer be compensated for by viscous flowing of the material. A consequence of this is a high polymerization shrinkage stress (PCS). On the other hand, a high viscosity is advantageous with regard to the rate of the radical reaction because a high viscosity promotes a fast curing of the materials. It is therefore difficult to reduce the PCS and simultaneously achieve a high reaction rate.

Furthermore, in the curing of dental materials, the volume contraction during polymerization is of decisive importance because the polymerization shrinkage can lead to marginal gap formation in filling composites. However, precisely monomers with high volume contraction display a large increase in the refractive index during polymerization, which is advantageous with regard to the sought reduction in translucence.

It was found according to the invention that, by the combination of monomers and the matching of the refractive index of the monomer mixture with that of the filler, an ideal compromise with respect to the named parameters can be achieved. In the uncured state, the materials have a high translucence and thus also allow the curing of thick layers. The translucence decreases during curing, with the result that the intrinsic colour of the dentine is masked and an optical adaptation to the tooth enamel is achieved.

The materials according to the invention preferably contain, as component (b), at least one monofunctional monomer or a mixture of monofunctional and polyfunctional monomers. Monofunctional monomers influence the network formation. By monofunctional monomers are meant compounds with one, by polyfunctional monomers compounds with two or more, preferably 2 to 4 and in particular 2, radically polymerizable groups.

For example, N-monosubstituted acrylamides, such as e.g. N-ethyl acrylamide, can be used as monofunctional monomers. Monofunctional monomers preferred according to the invention are monomethacrylates. Particularly preferred monofunctional methacrylates are methyl, ethyl, 2-hydroxyethyl, butyl, benzyl, tetrahydrofurfuryl and isobornyl methacrylate, p-cumyl-phenoxyethylene glycol methacrylate (CMP-1E) and mixtures thereof, quite particularly preferred are benzyl, tetrahydro-furfuryl or isobornyl methacrylate, CMP-1E and mixtures thereof. CMP-1E is the most preferred.

For example, N-disubstituted acrylamides, such as e.g. N,N-dimethyl acrylamide, and bisacrylamides, such as e.g. N,N'-diethyl-1,3-bis(acrylamido)-propane, 1,3-bis(methacrylamido)-propane, 1,4-bis(acrylamido)-butane or 1,4-bis (acryloyl)-piperazine can be used as polyfunctional monomers (a) and optionally (b). According to the invention, polyfunctional and in particular difunctional methacrylates are preferred, such as e.g. 1,6-bis-[2-methacryloyloxyethoxycarbonylamino]-2,2,4-trimethylhexane (UDMA; an addition product of 2-hydroxyethyl methacrylate and 2,2,4-trimethyl-hexamethylene diisocyanate), di-, tri- or tetraethylene glycol dimethacrylate, trime-thylolpropane trimethacrylate, pentaerythritol tetramethacrylate, as well as glycerol di- and trimethacrylate, 1,4-butanediol dimethacrylate, 1,10-decanediol dimethacrylate ($D_3MA$), 1,12-dodecanediol dimethacrylate and mixtures thereof.

Particularly preferred dimethacrylates are bisphenol-A-dimethacrylate, 2,2-bis[4-(2-hydroxy-3-methacryloyloxypropyl)-phenyl]propane (bis-GMA; an addition product of methacrylic acid and bisphenol-A-diglycidyl ether), ethoxylated or propoxylated bisphenol-A-dimethacrylate, such as e.g. the bisphenol-A-dimethacrylate 2-[4-(2-methacryloyloxyethoxyethoxy)phenyl]-2-[4-(2-methacryloyloxyethoxy) phenyl]propane) (SR-348c, Sartomer; 3 ethoxy groups), and 2,2-bis[4-(2-methacryloxypropoxy)-phenyl]propane, bis-(3-methacryloyloxymethyl)tricyclo-[$5.2.1.0^{2,6}$]decane (TCP) and mixtures thereof. Quite particularly preferred polyfunctional monomers are 2,2-bis[4-(2-methacryloxypropoxy) phenyl]propane, bis-GMA, SR-348c, TCP and mixtures thereof.

According to the invention, monomers and monomer mixtures are preferred which, in the uncured state, have a refractive index of from 1.50 to 1.70, preferably 1.50 to 1.60, wherein, in the case of monomer mixtures, those mixtures which exclusively contain monomers with a refractive index of from 1.50 to 1.70 and in particular 1.50 to 1.60 are particularly preferred. When combined with the fillers used according to the invention, composite pastes with high translucence are obtained. The preferred monomers display a large change in the refractive index during their polymerization, which leads to a clear reduction in the translucence, wherein monomers with a polymerization shrinkage of less than 10 vol.-%, in particular of from 5 to 9 vol.-% are preferred. Unless otherwise indicated, the polymerization shrinkage here is determined according to ISO standard 17304:2013.

The more electrons a molecule contains and the more polarizable these electrons are, the higher the refractive index of monomers is. The refractive index of polymers increases with the density and with increasing crystallinity and, in the case of organic polymers, is 1.29-1.73 (cf. H.-G. Elias, Makromoleküle-Anwendungen von Polymeren, Vol. 4. 6$^{th}$ edition, Wiley-VCH, Weinheim 2003, 513-515). Purely aliphatic or cycloaliphatic methacrylates usually have a refractive index of below 1.50, provided that no elements with a higher atomic number, e.g. sulphur or bromine, are contained. For example, UDMA has a refractive index ($n_D$) of 1.485 (polymer 1.510) and TEGDMA of 1.461 (polymer 1.508). By contrast, aromatic monomers display $n_D$ values above 1.50 and are therefore preferred as compovent (a) and (b). For example, the refractive index of propoxylated bis-GMA is 1.54 and that of CMPE-1E is 1.5525 (polymer 1.5793). Through the incorporation of heavy elements such as e.g. sulphur, bromine or iodine, the refractive index can be further increased. By mixing monomers with different refractive indices, the refractive index of the monomer mixture can be adapted to the refractive index of the fillers used.

Furthermore, those monomer mixtures which contain at least one low-volatile monomethacrylate, preferably in a quantity of 0-30 wt.-%, particularly preferably 5-30 wt.-%, quite particularly preferably 10-25 wt.-%, at least one highly viscous di-functional methacrylate, preferably in a quantity of 5-50 wt. %, particularly preferably 10-35%, and at least one low-viscosity dimethacrylate, preferably in a quantity of 5-30 wt.-%, particularly preferably 8-25%, are preferred. These percentages relate to the total mass of the monomer mixture. Monomer mixtures which exclusively contain the named monomers are particularly preferred. Here too, in all cases monomers with a refractive index of from 1.50 to 1.70 and/or a polymerization shrinkage ($\Delta V_p$) below 10 vol.-%, in particular 5-9 vol.-%, are preferred.

According to the invention, by low-volatile monomers are meant compounds with a boiling point >150° C. at normal pressure. The boiling point can e.g. be determined using a distillation apparatus. By highly viscous monomers are meant substances with a viscosity 5 Pa·s, preferably 5 to 10,000 Pa·s and particularly preferably 5 to 2,000 Pa·s, and by low-viscosity monomers are meant substances with a viscosity 3 Pa·s, preferably 100 to 3,000 mPa·s and particularly preferably 500 to 2,000 mPa·s, wherein the viscosity is determined using a capillary viscometer (low-viscosity) or rotational viscometer (highly viscous) at a temperature of 25° C.

Quite particularly preferred are mixtures of the monomethacrylate CMP-1E ($\Delta V_P$=7.3 vol.-%, $n_D$=1.5525) with the highly viscous bis-GMA ($\eta$=approx. 800 Pa·s, $\Delta V_P$=6.1 vol.-%, $n_D$=1.549) and the low-viscosity monomers SR-348c ($\eta$=550-1700 mPa·s, $\Delta V_P$=5.9 vol.-%, $n_D$=1.536) and/or TCP ($\eta$=approx. 1200 mPa·s, $\Delta V_P$=6.4 vol.-%, $n_D$=1.501). These mixtures are characterized by a particularly low cytotoxicity.

The materials according to the invention can additionally also contain one or more acidic monomers. Polymerizable carboxylic acids, such as 4-(meth)acryloyloxyethyltrimellitic acid; phosphonic acid monomers, such as 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxylphosphoryl)-2-oxa-butyl]-acrylic acid ethyl and -2,4,6-trimethylphenyl ester; as well as polymerizable phosphoric acid esters, such as 2-methacryloyloxyethyl dihydrogen phosphate, 10-methacryloyloxydecyl dihydrogen phosphate, 6-(methacrylamido)hexyl dihydrogen phosphate and 1,3-bis-(N-acryloyl-N-propyl-amino)-propan-2-yl-dihydrogen phosphate are particularly suitable as acidic monomers. Particularly suitable acidic monomers are 4-(meth)acryloyloxyethyltrimellitic acid, 2-[4-(dihydroxyphosphoryl)-2-oxa-butyl]-acrylic acid ethyl or -2,4,6-trimethylphenyl ester and 10-methacryloyloxydecyl dihydrogen phosphate. The acidic monomers improve the adhesion of the materials to the tooth and are therefore used, above all, for the preparation of self-adhesive composite cements. The acidic monomers content is preferably in the range of 0-15 wt.-%, particularly preferably 1-15 wt.-% (relative to the total mass of monomers).

The refractive index is a material constant which is dependent on the wavelength of the light used, the temperature, the pressure and the purity of the substance. Unless otherwise indicated, by refractive index is meant here the refractive index measured at 20° C. with the light of the yellow Na D line ($\lambda$=589 nm) ($n_D^{20}$ or $n_D$ for short). The refractive index of liquid monomers and monomer mixtures can be determined using an commercially available Abbe refractometer.

The refractive index of solid substances such as e.g. of inorganic filler powders or polymer powders is determined according to the immersion method. The substances are dispersed at 20° C. in liquids with different refractive indices (so-called immersion liquids). The greater the difference in the refractive index between liquid and solid is, the clearer the contours of the solid particles appear. If the refractive index of the liquid is now changed such that it comes closer to that of the solid, the particle contours become weaker and disappear completely when the refractive indices are equalized. Liquids with a known refractive index, e.g. mixtures of benzyl salicylate ($n_D^{20}$=1.536) and triacetin ($n_D^{20}$=1.431) or bromo-naphthalene ($n_D^{20}$=1.657), are suitable as immersion liquids. By varying the quantity ratios of these substances, the refractive index of the mixture can be adapted to that of the solid to be measured. When the refractive indices match, the refractive index of the immersion liquid is determined using a refractometer.

It is possible to establish whether the refractive indices of the solid and the immersion liquid match by observing the Becke line (Becke line test). This is a bright line of light which appears when a boundary surface is defocussed. The solid to be tested is placed into a liquid with a known refractive index and observed under a microscope with monochromatic light. If the test piece and the liquid have different refractive indices, a narrow, bright ring (Becke line) appears around each particle, which ring moves during focussing. This process is repeated in different liquids with differing refractive indices until no more Becke lines occur and thus the refractive indices of the test piece and the liquid match.

According to a first embodiment, the materials according to the invention exclusively contain filler(s) (d), wherein the refractive indices of filler and matrix are defined as described above, and optionally such fillers which do not scatter visible light and which therefore do not influence the translucence. Other fillers are not present.

According to a second embodiment, the materials according to the invention contain, in addition to the filler (d), additionally one or more fillers (e) with a refractive index which is lower than the refractive index of the matrix by 0.02 to at most 0.155, preferably by 0.03 to 0.055. The filler (e) thus has a lower refractive index than the filler (d). A filler mixture can likewise be used as filler (e), wherein filler (e) includes all fillers with a refractive index in the range of from $n_D^{matrix}-n_D^{filler(e)}$=0.02 to 0.155, preferably 0.03 to 0.055.

It was found that by a combination of filler (d) and filler (e) at the same filler content, the reduction in translucence during polymerization can be intensified. The reduction in translucence during polymerization depends on the quantity of filler and on the increase in the difference between the refractive indices. In the case of higher quantities of filler or a greater increase in the differences, the translucence decreases more markedly. The addition of the filler (e) opens up a further possibility for controlling the reduction in translucence. The lower its refractive index is in comparison with the main filler, the greater the effect of the filler (e) is.

As the refractive index of the filler (e) is lower than that of the filler (d), the difference from the refractive index of the uncured monomer mixture is greater, with the result that the filler (e) can lead to a reduction in the translucence of the uncured materials. For this reason, the proportion of the filler (e) in the total quantity of filler should not exceed 15 wt.-%. The quantity of the filler (e) is preferably in a range of from 0 to 15 wt.-%, particularly preferably 0 to 10 wt.-%, quite particularly preferably 0 to 5 wt.-% and in particular 1 to 5 wt.-%, relative to the total quantity of filler.

According to the second embodiment, those materials which exclusively contain filler(s) (d) and (e) and optionally such fillers which do not scatter visible light and which therefore do not influence the translucence are preferred according to the invention. Other fillers are not present.

In addition to the filler (d) and optionally the filler (e) as well as fillers which do not scatter visible light and which therefore do not influence the translucence, according to a further embodiment the materials according to the invention can also contain a minor proportion of filler which does not fall within any of these categories (filler f).

As filler (f) such fillers are used primarily which serve to influence certain properties of the materials in a targeted manner, such as e.g. the X-ray opacity. They are added only in the quantity necessary to achieve the desired effect.

Such fillers can have a disadvantageous effect on the reduction in the translucence during curing. If the refractive index of the filler (f) is higher than that of the matrix, during polymerization the refractive index of the monomer mixture comes closer to that of the filler, unlike in the case of the fillers (d) and (e), with the result that the difference between the refractive indices becomes smaller. In this case, the filler (f) neutralizes the effect of the fillers (d) and (e). The proportion of the filler (f) in the total quantity of filler is therefore preferably in the range of from 0 to 15.5 wt.-%, particularly preferably 0 to 9.7 wt.-% and quite particularly preferably 0 to 5.1 wt.-%. Filler (f) can be a mixture of different fillers. The total quantity of the fillers (e) and (f) is preferably at most 35 wt.-%, relative to the total quantity of filler.

The refractive index of the filler (f) is preferably higher than the refractive index of the matrix by at most 0.055. Particularly preferably, the refractive index $n_D^{filler(f)}$ of the filler (f) is in the range $(n_D^{matrix}-0.02)<n_D^{filler(f)}<(n_D^{matrix}+0.055)$, wherein filler (f) only includes the filler which does not fall within one of the other filler categories.

In all embodiments, the quantity of filler which does not scatter visible light and does not influence the translucence in each case is preferably in the range of from 0 to 10 wt.-%, particularly preferably 0 to 1.8 wt.-%, relative to the total quantity of filler.

The fillers (d), (e) and (f) are in each case selected from the materials defined in the following. The assignment to a filler group is based on the refractive index and its difference from the refractive index of the matrix.

The dental materials according to the invention can contain organic or preferably inorganic or organic-inorganic fillers, wherein particulate fillers are preferred. Preferred inorganic particulate fillers are powders of X-ray opaque glasses with an average particle size of from 0.01 to 15 μm, preferably 0.10 to 5.0 μm; X-ray opaque fillers, such as ytterbium trifluoride, with an average particle size of from 0.050 to 2.0 μm, preferably 0.10 to 1.0 μm; mixed oxides of $SiO_2$, $ZrO_2$, ZnO and/or $TiO_2$ with an average particle size of from 5 to 500 nm, preferably 20 to 200 nm; nanoparticulate fillers, such as tantalum(V) oxide, barium sulfate or mixed oxides of $SiO_2$ with ytterbium(III) oxide or tantalum (V) oxide with an average particle size of from 5 to 500 nm, preferably 20 to 200 nm.

By organic-inorganic fillers are meant polymer particles which, for their part, are filled with inorganic fillers. Organic-inorganic fillers with an average particle size of from 5 to 100 μm, preferably of from 10 to 50 μm are preferred. In the case of organic-inorganic fillers, the refractive index of the cured polymer matrix is preferably selected such that it matches the refractive index of the inorganic filler contained in it, with the result that the filler particles have a high translucence in the matrix.

Organic-inorganic fillers are preferably prepared by thermal curing of composite pastes based on dimethacrylate mixtures and fillers. Bis-GMA, UDMA and $D_3MA$ are preferably used as dimethacrylates. X-ray opaque glass fillers and/or ytterbium trifluoride preferably serve as fillers. The refractive index of the polymerized monomer mixture is preferably set such that it corresponds to the refractive index of the main filler used. The thermal polymerizates are then ground and used as powder.

All particle sizes are weight averages. The light scattering reduces as the particle size reduces, but fillers with a small particle size have a greater thickening effect. According to the invention, fillers with a particle size in the range of from 100 nm to 5 μm and in particular in the range of from 200 nm to 2 μm are therefore preferred.

The X-ray opaque glasses preferably have a refractive index of 1.51-1.55, $YbF_3$ has a refractive index of 1.545 and the refractive index of the remaining fillers, such as e.g. the organic-inorganic fillers, is preferably in the range of from 1.48 to 1.54.

In addition to the named fillers, the materials can contain fillers with a particle size of preferably <50 nm, particularly preferably <40 nm. The particle size is preferably in the range of 10-50 nm and particularly preferably of 10-40 nm. Because of their small particle size, these fillers do not scatter visible light and thus have no influence on the translucence. Preferred examples of these fillers are pyrogenic silica and precipitated silica. These have a refractive index of approx. 1.46.

The fillers are preferably surface-modified, particularly preferably by silanization, in particular using 3-methacryloyloxypropyltrimethoxysilane. The silanization has no measurable influence on the refractive index of the filler.

The dental materials according to the invention display a reduction in translucence during polymerization which is to be attributed to an increase in the difference between the refractive index of the polymerizable matrix and that of the filler. This requires the refractive indices of the monomer(s) and the filler to be matched. The type, quantity and refractive indices of the monomer or of the monomer mixture and of the filler or the fillers are preferably selected such that the material has a translucence of from 15 to 80%, preferably 20 to 75%, before the polymerization. To determine the translucence of cured materials, polymer or composite test pieces (round discs with a diameter of 20 mm and a thickness of 1 mm) are prepared and measured colorimetrically in a spectrophotometer (colour measurement in transmission, wavelength 360-740 nm). In the case of uncured materials, the composite paste or the monomer mixture is measured colorimetrically in a glass vessel with a layer thickness of 1 mm. The CM-5 Spectrophotometer from Minolta is preferably used to determine the translucence.

The dental materials according to the invention preferably contain 20 to 80 wt.-%, particularly preferably 40 to 80 wt.-% X-ray opaque glass or glasses. Ytterbium fluoride is preferably used in a quantity of from 0 to 40 wt.-%, particularly preferably 0 to 30 wt.-%, mixed oxides preferably in a quantity of from 0 to 70 wt.-%, particularly preferably 0 to 40 wt.-%. Organic-inorganic fillers, so-called composite fillers or isofillers, are preferably used in a quantity of 0 to 50 wt.-% and particularly preferably of from 0 to 30 wt.-%. Materials which contain 49 to 61 wt.-% X-ray opaque glass or glasses, 2.5 to 6 wt.-% $YbF_3$, 0 to 10 wt.-% mixed oxide(s) and 7 to 17 wt.-% isofillers are quite particularly preferred. The total quantity of all fillers is preferably in the range of from 5 to 90 wt.-%, particularly preferably 10 to 85 wt.-% and quite particularly preferably 40 to 80 wt.-%. All quantities relate to the total mass of the material.

Preferably, when mixtures of the named fillers are used, the weight ratio of X-ray opaque glasses to ytterbium fluoride is in the range of from 10:0 to 10:2, the weight ratio of X-ray opaque glasses to mixed oxides is in the range of from 10:0 to 10:5 and the weight ratio of X-ray opaque glasses to organic-inorganic fillers is in the range of from 10:0 to 1:1. Filler mixtures which contain at least 50 wt.-% of at least one X-ray opaque glass, relative to the total mass of fillers, are particularly preferred.

The compositions according to the invention are preferably cured by irradiation with blue light (wavelength range of 400-500 nm), preferably by irradiation with an LED lamp or halogen lamp. For this, the materials preferably contain at least one photoinitiator which is active in the specified wavelength range.

Preferred photoinitiators are photosensitizers, above all of α-diketones, such as 9,10-phenanthrenequinone, 1-phenyl-propane-1,2-dione, diacetyl or 4,4'-dichlorobenzil or derivatives thereof, particularly preferably camphorquinone (CQ) and derivatives thereof, and mixtures thereof.

The photoinitiators are preferably used in combination with accelerators. Tertiary amines, such as e.g. tertiary aromatic amines, in particular N,N-dialkylanilines, -p-toluidines or -3,5-xylidines, p-(N,N-dialkylamino-phenyletha-nol, -benzoic acid derivatives, -benzaldehydes, -phenylacetic acid esters and -phenylpropionic acid esters are particularly suitable as accelerators. Specific examples of these are N,N-dimethyl-aniline, N,N-dimethyl-p-toluidine, N,N-3,5-tetramethylaniline, N,N-dimethylamino-p-benzaldehyde, p-(dimethylamino)-benzoic acid ethyl ester or p-(dimethylamino)benzonitrile. Also suitable are tertiary aliphatic amines, such as e.g. tri-n-butylamine, dimethylaminoethan-2-ol, triethanolamine, dimethylaminoethyl methacrylate, N,N-dimethylbenzylamine, or heterocyclic amines, such as e.g. 1,2,2,6,6-pentamethylpiperidine, and amino acid derivatives, such as e.g. N-phenylglycine.

In compositions which contain acidic monomers, such as e.g. self-adhesive composites, amine-free accelerators are preferably used, such as e.g. sulfinic acids and sulfinates, borates, enolates, phosphines or other compounds which contain active hydrogen atoms, e.g. heterocyclic compounds such as morpholine derivatives or 1,3-dioxolanes.

Particularly preferred photoinitiators are acyl- or bisacyl-germanium compounds, in particular the monoacyltrialkyl- and bisacyldialkylgermanium compounds disclosed in EP 1 905 413 A1, such as e.g. benzoyltrimethylgermanium, bis-benzoyldiethyl-germanium or bis-(4-methoxybenzoyl)di-ethylgermanium. Acyl- and bisacylgermanium compounds have the advantage that they lose their colour after the irradiation (bleaching effect) and thus do not impair the transparency of the cured materials. In addition, they are monomolecular photoinitiators, i.e. they do not need an accelerator in order to achieve their full activity.

Further particularly preferred photoinitiators are acyl- or bisacylphosphine oxides, in particular the compounds described in EP 0 007 505, EP 0 073 413, EP 0 184 095 and EP 0 615 980. Preferred examples are the commercially available compounds 2,4,6-trimethylbenzoyl diphenylphosphine oxide (Lucirin® TPO, BASF) and bis(2,4,6-trimethylbenzoyl)phenylphosphine oxide (Irgacure® 819, Ciba). Acyl- and bisacylphosphine oxides likewise belong to the group of monomolecular photoinitiators and are characterized by a low self-absorption.

Optionally, the compositions used according to the invention can contain further additives, above all stabilizers, such as e.g. polymerization stabilizers, dyes, antibacterial active ingredients, fluoride-ion-releasing additives, optical brighteners, fluorescent agents, UV absorbers, substances for improving the fracture toughness and/or effect agents.

The dental materials according to the invention preferably have a photosensitivity of greater than 60 s, particularly preferably 80 s to 300 s. By photosensitivity is meant the time during which the materials can be processed without premature curing by ambient light, such as e.g. the dentist's surgical light. The photosensitivity is determined according to ISO 4049: 2000: "Dentistry—Polymer-based filling, restorative and luting materials". For this, a material sample is irradiated using a xenon lamp at 8000 lx until the onset of polymerization. The photosensitivity is the time in seconds until the oneset of polymerization. At a photosensitivity of 60 s, the material begins to cure after 60 s under the xenon lamp. The photosensitivity can be set via the addition of polymerization inhibitors, preferably of anaerobic inhibitors.

Furthermore, the dental materials according to the invention preferably have an X-ray opacity of from 100% to 500% Al, particularly preferably 150% to 300% Al. The X-ray opacity is likewise determined according to the above-named ISO standard 4049. A test piece from the polymerized dental material together with an aluminium step wedge with a step height of 1 mm is photographed using an X-ray camera. The degree of blackening of the images is compared and the X-ray opacity is indicated in % Al, 100% X-ray opacity corresponds to the blackening of 1 mm aluminium. The X-ray opacity can be set via the quantity of X-ray opaque fillers, such as X-ray opaque glasses or ytterbium (III) fluoride. The X-ray opacity is an important clinical property of filling composites which enables the dentist e.g. to detect fillings on X-ray photographs.

According to the invention, those dental materials are particularly preferred which contain:

(1) 1 to 50 wt.-%, preferably 5 to 40 wt.-% and quite particularly preferably 5 to 25 wt.-% polyfunctional radically polymerizable monomer(s), (2) 1 to 20 wt.-%, preferably 2 to 15 wt.-% and quite particularly preferably 3 to 10 wt.-% further radically polymerizable monomer(s), (3) 0.01 to 5.0 wt.-%, preferably 0.1 to 3.0 wt.-% and quite particularly preferably 0.1 to 2.0 wt.-% photoinitiator, (4) 5 to 90 wt.-%, preferably 10 to 85 wt.-% and quite particularly preferably 40 to 80 wt.-% filler(s), and optionally (5) 0.1 to 5.0 wt.-%, preferably 0.1 to 2.0 wt.-% and quite particularly preferably 0.2 to 1.5 wt.-% additive(s).

Unless otherwise indicated, all values here relate to the total mass of the dental material. The quantity of filler comprises the total quantity of all fillers, wherein the quantities of the individual filler components are as defined above.

Those dental materials which consist of the named substances are particularly preferred. Furthermore preferred are those materials in which the individual substances in each case are selected from the above-named preferred and particularly preferred substances.

The dental materials according to the invention are particularly suitable as dental cements, filling composites, coating and veneering materials as well as materials for manufacturing inlays, onlays, crowns and bridges, quite particularly as so-called bulk fill composites. By bulk fill composites are meant dental filling materials which can be cured with light even at layer thicknesses of more than 3 mm, preferably more than 4 mm and in particular of 4-5 mm. They also enable the preparation of larger tooth fillings with only 1 to 2 layers.

The dental materials are suitable primarily for intraoral application by the dentist to restore damaged teeth (clinical materials). However, they can also be used extraorally, for example in the manufacture or repair of dental restorations (technical materials).

The invention is described in further detail in the following with reference to examples.

EXAMPLES

Examples 1 to 3

Preparation of Light-Curing Composite Materials

Composites with the monomer mixtures described in Table 1 were prepared. The compositions of the composites are indicated in Table 2. The components were mixed with each other using a kneader (Linden) or a mixer (Speedmixer, FlackTek Inc.). To determine the translucence of the composites, in each case cured test pieces were prepared (round, Ø 20 mm, h=1 mm) and colorimetrically measured using a spectrophotometer (CM-5 Spectrophotometer, Minolta). The polymerization was carried out using an LED lamp (Bluephase, Ivoclar Vivadent AG, 10 s at 1000 mW/cm$^2$). The bending strength and the through-curing depth were measured according to ISO 4049:2009: Dentistry—polymer-based restorative materials. The polymerization shrinkage (vol.-%) was determined according to ISO 17304:2013. The flexural modulus was calculated in a known manner from the gradient of the measurement curve for the bending strength. The determined properties of the composite pastes are shown in Table 3.

Example 1 shows that cured composites with a low translucence (high opacity) can be prepared from composite pastes with high translucence at large through-curing depth. Example 2 shows that the effect of the reduction in translucence during polymerization can be clearly intensified by the addition of a low refractive index glass filler (G018-090). The composite in Example 3 has an advantageous combination of properties.

TABLE 1

Composition of the monomer mixtures (values in wt.-%)

| Constituent | No. 1 | No. 2 | No. 3 |
|---|---|---|---|
| Ethoxylated p-cumylphenol methacrylate (CMP-1E) | 20% | 20% | 20% |
| Bisphenol A dimethacrylate with 3 ethoxy groups (SR-348C)[1] | 48.95% | 11.8% | 48.563% |
| Bis-GMA | 20% | 23.8% | 20% |
| Urethane dimethacrylate (UDMA) | — | 23.5% | — |
| Bis-(3-methacryloyloxymethyl)-tricyclo[5.2.1.0$^{2,6}$]decane (TCP) | 10% | — | 10% |
| 2,2-Bis[4-2-methacryloxypropoxy)-phenyl]propane[2] | — | 20% | — |
| Camphorquinone | 0.2% | 0.2% | 0.2% |
| (4-Dimethylamino)-benzoic acid ethyl ester (EMBO) | 0.8% | 0.8% | 0.8% |
| Bis(4-methoxybenzoyl)diethyl-germanium[3] | 0.05% | 0.1% | 0.05% |
| Stabilizer, additives | — | — | 0.387% |
| Refractive index of the mixture (uncured) | 1.5416 | 1.5308 | 1.5416 |
| Refractive index of the mixture (cured) | 1.5683 | 1.550 | 1.5683 |

[1]CAS 41637-38-1
[2]CAS 24447-72-1
[3]CAS 1469766-31-1 (Ivocerin ®, Ivoclar Vivadent AG)

TABLE 2

Composition of the composites (values in wt.-%)

| Constituent | Ex. 1 | Ex. 2 | Ex. 3 |
|---|---|---|---|
| Monomer mixture 1 | 25% | — | — |
| Monomer mixture 2 | — | 30% | — |
| Monomer mixture 3 | — | — | 30% |
| Barium aluminium silicate glass filler (Ø = 1.5 μm)[1] | 75% | 60% | 18% |
| Strontium aluminium silicate glass filler (Ø = 1.0 μm)[2] | — | 10% | — |
| Barium aluminium silicate glass filler (Ø = 8 μm)[1] | — | — | 36% |
| Ytterbium fluoride (YbF$_3$) | — | — | 4% |
| Particulate composite material (Ø = 30 μm)[3] | — | — | 12% |

[1]Dental glass GM 27884 (Schott), refractive index = 1.53 (Ø = average particle size, weight average)
[2]Dental glass G018-090 (Schott), refractive index = 1.50
[3]polymerized, ground composite material consisting of monomer matrix, glass filler GM27884 and YbF$_3$; refractive index = 1.53

TABLE 3

Properties of the composites

| Ex. | Through-curing depth[1] | Transparency before polymerization | Transparency 10 min after polymerization | Transparency 24 h after polymerization | Bending strength[1] | Flexural modulus | ΔV$_p$[1] |
|---|---|---|---|---|---|---|---|
| 1 | 6.8 mm[2] | 46.3% | 9.5% | 9.2% | — | — | — |
| 2 | 8.2 mm[2] | 41.3% | 10.7% | — | — | — | — |
| 3 | 8.07 mm[2] | 31% | 10.07% | 9.89% | 117.2 MPa | 8.6 GPa | 3.48% |

[1]ΔV$_p$ = polymerization shrinkage according to ISO17304: 2013
[2]measured value

The invention claimed is:

1. Radically polymerizable dental material which comprises
   (a) 5 to 40 wt.-% of at least one polyfunctional radically polymerizable monomer,
   (b) 2 to 15 wt.-% of at least one monofunctional radically polymerizable monomer,
   (c) 0.1 to 3.0 wt.-% of at least one photoinitiator for the radical polymerization and 10 to 85 wt.-% of at least one filler,
characterized in that the dental material comprises at least one filler (d) and that the mixture of the monomers (a) and (b) has a refractive index of from 1.50 to 1.70 and in that the refractive index of the monomer mixture before the curing corresponds to the refractive index of the filler used or is higher by up to 0.013 and after the curing is higher than the refractive index of the filler (d) by at least 0.02, and in that the dental material in addition to the filler (d) comprises, relative to the total quantity of filler, 0 to 15 wt.-% of at least one filler (e) having a refractive index which is lower than the refractive index of the mixture of the monomers (a) and (b) by 0.02 to maximally 0.155, 0 to 10 wt.-% of at least one filler which does not scatter visible light and does not influence the translucence, and maximally 15.5 wt.-% of filler (f) which does not fall within any of the filler categories.

2. Dental material according to claim 1, which comprises, as component (a), at least one polyfunctional methacrylate, 1,6-bis-[2-methacryloyloxy-ethoxycarbonylamino]-2,2,4-trimethylhexane (an addition product of 2-hydroxyethyl methacrylate and 2,2,4-trimethyl-hexamethylene diisocyanate), di-, tri- or tetraethylene glycol dimethacrylate, trimethylolpropane trimethacrylate, pentaerythritol tetramethacrylate, glycerol di- and trimethacrylate, 1,4-butanediol dimethacrylate, 1,10-decanediol dimethacrylate ($D_3MA$), 1,12-dodecanediol dimethacrylate and mixtures thereof, bisphenol-A-dimethacrylate, 2,2-bis[4-(2-hydroxy-3-methacryloyloxy-propyl)phenyl]propane (an addition product of methacrylic acid and bisphenol-A-diglycidyl ether), ethoxylated or propoxylated bisphenol-A-dimethacrylate, 2-[4-(2-methacryloyloxyethoxyethoxy)phenyl]-2-[4-(2-methacryloyloxy-ethoxy)phenyl]propane), 2,2-bis[4-(2-methacryloxypropoxy)-phenyl]propane, or bis-(3-methacryloyloxymethyl)tricyclo-[$5.2.1.0^{2,6}$]decane or a mixture thereof.

3. Dental material according to claim 1, which exclusively contains, as component (a) and/or component (b), monomers with a refractive index of from 1.50 to 1.70.

4. Dental material according to claim 1, which comprises at least one low-volatile monomethacrylate, in a quantity of 5-30 wt.-%, at least one highly viscous difunctional methacrylate, in a quantity of 5-50 wt.-%, and at least one low-viscosity dimethacrylate, in a quantity of 5-30 wt.-%, wherein the percentages relate to the total mass of the monomer mixture in each case.

5. Dental material according to claim 1, in which the refractive index of the further filler not falling within any of the categories is higher than the refractive index of the mixture of the monomers (a) and (b) by at most 0.055.

6. Dental material according to claim 1, which comprises, as filler, a pulverulent X-ray opaque glass with an average particle size of from 0.01 to 15 µm, an X-ray opaque filler, ytterbium trifluoride, a mixed oxide of $SiO_2$, $ZrO_2$, $ZnO$ and/or $TiO_2$, nanoparticulate tantalum(V) oxide, barium sulfate, a mixed oxide of $SiO_2$ with ytterbium(III) oxide or tantalum(V) oxide, pyrogenic silica or precipitated silica, an organic polymer powder, organic-inorganic filler or a mixture thereof.

7. Dental material according to claim 1, which comprises, as component (c), an α-diketone, 9,10-phenanthrenequinone, 1-phenyl-propane-1,2-dione, diacetyl or 4,4'-dichlorobenzil or a derivative thereof, camphorquinone (CQ) or a derivative thereof, optionally in combination with an accelerator, or a mixture thereof and/or an acyl- or bisacylgermanium compound and/or an acyl- or bisacylphosphine oxide.

8. Dental material according to claim 1, which comprises, as further component, at least one additive which is selected from stabilizers, polymerization stabilizers, dyes, antibacterial active ingredients, fluoride-ion-releasing additives, optical brighteners, fluorescent agents, UV absorbers, substances for improving the fracture toughness and/or effect agents.

9. Dental material according to claim 1, which further comprises (5), 0.1 to 5.0 wt.-% additive(s).

10. Process of using the dental material according to claim 1 comprising preparing a dental cement, filling composite, coating material, veneering material or bulk fill composite with the dental material and using the prepared material in a dental application.

11. Process according to claim 10 wherein the dental material is fabricated into inlays, onlays, crowns or bridges.

12. Dental material according to claim 1, in which the further filler (e) has a refractive index of which is lower than the refractive index of the mixture of the monomers (a) and (b) by 0.03 to 0.055.

13. Dental material according to claim 1, which comprises
(1) 5 to 40 wt.-% polyfunctional radically polymerizable monomer(s),
(2) 2 to 15 wt.-% monofunctional radically polymerizable monomer(s),
(3) 0.1 to 3.0 wt.-% photoinitiator,
(4) 10 to 85 wt.-% filler(s), and optionally
(5) 0.1 to 2.0 wt.-% additive(s).

14. Dental material according to claim 1, which comprises
(1) 5 to 25 wt.-% polyfunctional radically polymerizable monomer(s),
(2) 3 to 10 wt.-% monofunctional radically polymerizable monomer(s),
(3) 0.1 to 2.0 wt.-% photoinitiator,
(4) 40 to 80 wt.-% filler(s), and optionally
(5) 0.2 to 1.5 wt.-% additive(s).

15. Dental material according to claim 1, wherein the at least one monofunctional monomer component comprises a methacrylate, methyl, ethyl, 2-hydroxyethyl, butyl, benzyl, tetrahydrofurfuryl or isobornyl methacrylate, p-cumyl-phenoxyethylene glycol methacrylate (CMP-1E) or a mixture thereof.

* * * * *